United States Patent
Müller et al.

(10) Patent No.: US 12,137,930 B2
(45) Date of Patent: Nov. 12, 2024

(54) SYSTEM OF SONOTRODE AND GUIDE SHAFT

(71) Applicant: Woodwelding AG, Stansstad (CH)

(72) Inventors: Andrea Müller, Winterthur (CH); Andrè Schwery, Rombach (CH)

(73) Assignee: WOODWELDING AG, Stansstad (CH)

( * ) Notice: Subject to any disclaimer, the term of this patent is extended or adjusted under 35 U.S.C. 154(b) by 134 days.

(21) Appl. No.: 16/967,869

(22) PCT Filed: Feb. 6, 2019

(86) PCT No.: PCT/EP2019/052868
§ 371 (c)(1),
(2) Date: Aug. 6, 2020

(87) PCT Pub. No.: WO2019/154833
PCT Pub. Date: Aug. 15, 2019

(65) Prior Publication Data
US 2021/0045767 A1  Feb. 18, 2021

(30) Foreign Application Priority Data
Feb. 8, 2018 (CH) .................................. 00150/18

(51) Int. Cl.
| A61B 17/16 | (2006.01) |
| A61B 17/32 | (2006.01) |
| A61B 17/00 | (2006.01) |
| A61B 17/22 | (2006.01) |

(52) U.S. Cl.
CPC .. *A61B 17/320068* (2013.01); *A61B 17/1613* (2013.01); *A61B 2017/00955* (2013.01);
(Continued)

(58) Field of Classification Search
CPC .......... A61B 2017/320074; A61B 17/320068; A61B 17/22004; A61B 2017/00106;
(Continued)

(56) References Cited

U.S. PATENT DOCUMENTS

| 5,346,502 A | 9/1994 | Estabrook et al. |
| 5,358,505 A * | 10/1994 | Wuchinich ............... A61N 7/00 |
| | | 606/99 |

(Continued)

FOREIGN PATENT DOCUMENTS

| CN | 107249489 A | 10/2017 |
| CN | 107466225 A | 12/2017 |

(Continued)

OTHER PUBLICATIONS

English translation of Chinese Office Action dated Oct. 18, 2023, Application No. 2019800118112; 7 pages.
(Continued)

*Primary Examiner* — Shaun L David
*Assistant Examiner* — Mitchell Brian Hoag
(74) *Attorney, Agent, or Firm* — Rankin, Hill & Clark LLP

(57) ABSTRACT

A system to be used for transmitting ultrasonic vibration, the system including a sonotrode designed to vibrate in a stationary wave having at least one node position between the distal end and the proximal end of the sonotrode, and a guide shaft with a through opening. During operation the sonotrode extends through the through opening of the guide shaft and the distal end of the guide shaft is situated on a distal side of the most distal node position of the sonotrode. The sonotrode and the guide shaft are adapted to each other for radial clearance between the sonotrode and the guide shaft to be a minimum for a sonotrode portion comprising the most distal node position.

18 Claims, 3 Drawing Sheets

(52) U.S. Cl.
CPC ... *A61B 17/22004* (2013.01); *A61B 17/22012* (2013.01); *A61B 2017/320074* (2017.08)

(58) Field of Classification Search
CPC ...... A61B 2017/00924; A61B 17/2204; A61B 2017/22007–22011; A61B 2017/22017; A61B 17/22012; A61B 2017/320069–320077; A61B 18/0206; A61B 2090/3925; A61F 9/00745; A61F 2002/2864; A61F 2002/4683; A61F 2013/15869; A61N 7/00
USPC ......................................................... 606/169
See application file for complete search history.

(56) References Cited

U.S. PATENT DOCUMENTS

| | | | | |
|---|---|---|---|---|
| 5,664,570 | A * | 9/1997 | Bishop | G10K 15/043 |
| | | | | 601/2 |
| 9,198,703 | B2 * | 12/2015 | Giersch | A61B 17/8872 |
| 9,301,790 | B2 * | 4/2016 | Dorawa | A61B 17/864 |
| 9,510,886 | B2 * | 12/2016 | Giersch | A61B 17/864 |
| 2005/0096679 | A1 * | 5/2005 | Stulen | A61B 17/320068 |
| | | | | 606/169 |
| 2007/0106158 | A1 * | 5/2007 | Madan | A61B 17/320068 |
| | | | | 600/459 |
| 2009/0036912 | A1 * | 2/2009 | Wiener | A61B 17/30 |
| | | | | 606/169 |
| 2009/0318944 | A1 * | 12/2009 | Kimura | A61B 17/320068 |
| | | | | 606/169 |
| 2012/0143261 | A1 * | 6/2012 | Giersch | A61B 17/864 |
| | | | | 606/304 |
| 2015/0257780 | A1 * | 9/2015 | Houser | A61B 17/320092 |
| | | | | 606/109 |
| 2016/0332362 | A1 | 11/2016 | Vogler et al. | |
| 2016/0374708 | A1 | 12/2016 | Wiener et al. | |
| 2017/0143399 | A1 * | 5/2017 | Sakai | H01L 41/1873 |
| 2017/0197231 | A1 | 7/2017 | Knorr | |
| 2017/0239497 | A1 * | 8/2017 | Yoshimine | A61B 18/00 |
| 2018/0055530 | A1 * | 3/2018 | Messerly | H10N 30/50 |
| 2018/0146975 | A1 * | 5/2018 | Zhang | A61N 7/00 |
| 2019/0201047 | A1 * | 7/2019 | Yates | G16H 50/20 |
| 2019/0247080 | A1 * | 8/2019 | Yokoyama | A61B 17/16 |
| 2019/0314051 | A1 * | 10/2019 | Li | A61B 17/3211 |
| 2020/0253631 | A1 * | 8/2020 | Apperson | A61B 17/320068 |
| 2020/0305923 | A1 * | 10/2020 | Maeda | A61B 17/320068 |

FOREIGN PATENT DOCUMENTS

| | | |
|---|---|---|
| DE | 3707403 | 9/1987 |
| EP | 1 790 303 | 5/2007 |
| JP | 2508203 Y2 | 8/1996 |
| JP | 2001-8943 A | 1/2001 |
| JP | 2012-223582 A | 11/2012 |
| WO | 98/14126 A1 | 4/1998 |
| WO | 2009/109057 A1 | 9/2009 |
| WO | 2011/054123 | 5/2011 |
| WO | 2017/119099 | 7/2017 |

OTHER PUBLICATIONS

Chinese Search Report dated Oct. 16, 2023, Application No. 2019800118112; 3 pages.

* cited by examiner

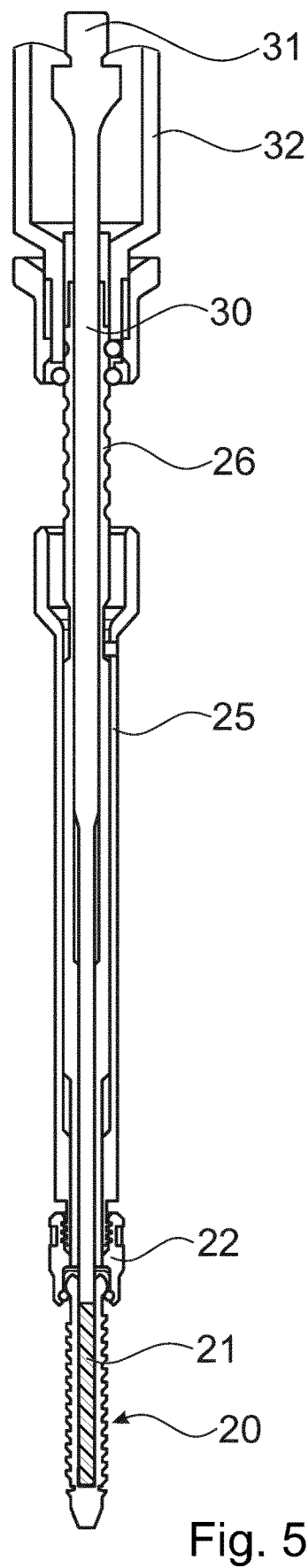
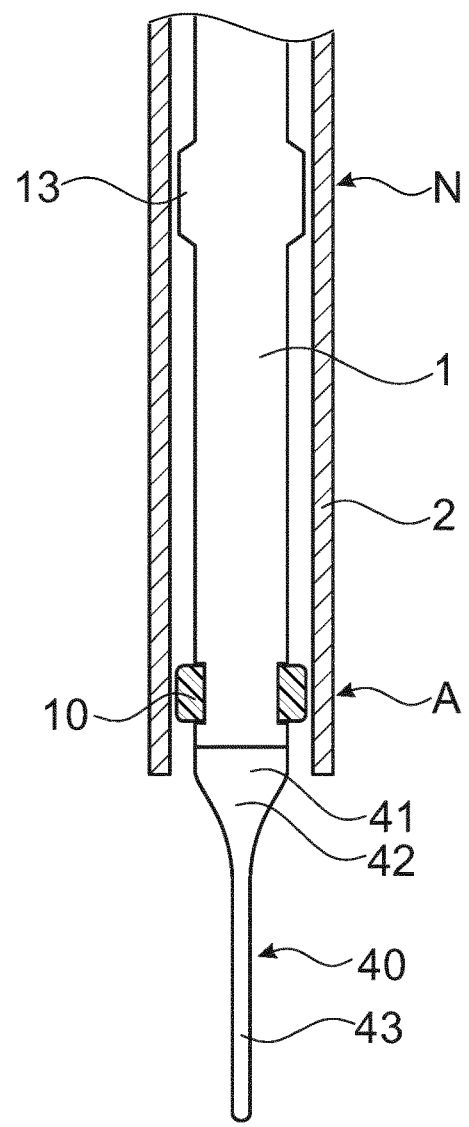
Fig. 5
Fig. 6

SYSTEM OF SONOTRODE AND GUIDE SHAFT

BACKGROUND OF THE INVENTION

Field of the Invention

The invention relates to a system including a sonotrode and a guide shaft and to a sonotrode suitable for the system, wherein sonotrode and guide shaft are adapted to each other for enabling operation of the sonotrode when at least part of the sonotrode length is positioned to extend through the guide shaft. The system is suitable for use in a device in which ultrasonic vibration is produced, e.g., by a transducer unit, and is transmitted through the sonotrode to a distal end thereof to be applied to an object or to a medium for achieving a desired effect. The system according to the invention is in particular suitable for applications in which the sonotrode distal end is to vibrate longitudinally, in which the sonotrode is slender and long, and in which a large portion of the sonotrode length is to extend in the guide shaft. This is the case, e.g., in the medical field of minimally invasive surgery, for which the transducer unit, e.g., being contained in an ultrasonic hand piece, is positioned outside of a patient, and the sonotrode is coupled to the transducer unit and has to reach through tissue to a target site within the patient, wherein the tissue through which the sonotrode is to reach is to be kept unaffected by the vibration with the aid of the guide shaft and the tissue opening through which the sonotrode is to reach is to be as small as possible.

Description of Related Art

WO2011/054123 discloses a system suitable for anchoring a permeable sleeve (in particular a cannulated bone screw) in hard tissue with the aid of a thermoplastic element. For achieving this anchorage, the thermoplastic element is positioned in the permeable sleeve, the permeable sleeve is coupled to an ultrasonic hand piece and is in situ liquefied and at least partly pressed through the permeable sleeve by the sonotrode of the hand piece being pressed against a proximal face of the thermoplastic element. The ultrasonic hand piece includes a housing in which a transducer unit and, coupled thereto, the sonotrode, and a driver spring are arranged, such that the combination of transducer unit and sonotrode is axially moveable within the housing in a limited manner and is acoustically decoupled from the housing, such that a distal end of the sonotrode is able to protrude from a distal housing end, and such that the driver spring, acting between a proximal housing portion and the transducer unit, biases the combination of transducer unit and sonotrode away from the proximal end of the housing. In an assembled configuration of the system, in which the permeable sleeve with the thermoplastic element positioned therein is coupled to the distal end of the housing, the system parts form a closed load frame in which the thermoplastic element is compressed between the distal face of the sonotrode and the permeable sleeve, and in which the sonotrode is completely encased by the housing and the permeable sleeve, being supported by two sliding bushes arranged on the inner surface of a distal housing part.

The publication EP1790303 (Olympus) discloses an ultrasonic treatment apparatus including a sonotrode arranged in a guide tube, a distal sonotrode end protruding from the guide tube and being shaped for treating tissue. At a node position of the sonotrode a support member made of silicone rubber is mounted in the guide tube. In a similar manner, publications DE 3707403, US2016/00374708 and EP3401025 disclose sonotrode arrangements in which the sonotrode carries elastic and/or abrasion-resistant rings in node positions. Publication U.S. Pat. No. 5,346,502 discloses a sonotrode extending in a polymeric sheath, which in node positions is in contact with the sonotrode (no radial clearance).

The full disclosure of all the publications cited above is incorporated herein by reference.

SUMMARY OF THE INVENTION

It is the object of the present invention to improve the system of sonotrode and guide shaft as known from the state of the art to make it better suitable for operation in cases in which the vibrating sonotrode is to be axially moved in the guide shaft, in which the sonotrode is slender and long, i.e., has a comparatively small bending strength, in which the sonotrode extends over a large portion of its length, in particular over its full length, in the guide shaft, in which the guide shaft is as slender as possible and possibly includes more than one piece and therefore radial clearance between sonotrode and guide shaft is small and coaxiality possibly not fully guaranteed. In this named system of sonotrode and guide shaft, transmission of vibrational energy though the sonotrode is to be as efficient as possible and friction between sonotrode and guide shaft as low as possible. Such friction and corresponding friction wear not only constitute an undesirable loss of energy and generation of heat in undesirable locations, and shortens the life span of the system but it is furthermore to be prevented because, in particular in medical applications, wear debris, in particular metal debris, may prove harmful for neighboring tissue. Furthermore, the measures according to the invention with which the named object is achieved are to be technically simple, in particular possible for the through opening of the guide shaft having a constant cross section.

The sonotrode of the system according to the invention, the same as known sonotrodes, is preferably designed to be adapted to a vibration frequency, e.g., in the range of 20 to 40 kHz and for vibrating substantially longitudinally in a stationary wave with anti-node positions (positions with maximum amplitude) at both ends. This means that the sonotrode has a length that corresponds to an integer multiple of half the wave length ($\lambda/2$) of the stationary wave, and that there is at least one node position (position of minimum amplitude) between the two sonotrode ends.

The above stated objects are achieved in the system according to the invention by providing, in an axial position of the system in which the most distal node position of the sonotrode is situated, a region in which radial clearance between sonotrode and guide shaft is at a minimum. This is realized by the sonotrode including, in the most distal node position an increased cross section, and by the through opening of the guide shaft portion extending form the distal end portion to beyond the most distal node position of the sonotrode including a constant cross section. Adjoining the sonotrode portion of increased cross section (most distal node position) in distal and in proximal direction are sonotrode portions of lesser cross section (larger radial clearance), wherein transition between the differing cross sections may include a step or may be a gradual transition, and wherein the cross section of the sonotrode portion on the distal side of the portion of increased cross section may be smaller than the cross section of the sonotrode on the proximal side of the portion with increased cross section. This means that radial clearance between sonotrode and guide shaft is greatest for the sonotrode portion extending through the most distal portion of the guide shaft, is reduced in the most distal node position of the sonotrode and is again greater for a proximally adjoining sonotrode portion but possibly not as great as for the most distal portion.

The sonotrode is preferably made of a metal, e.g., titanium, and the guide shaft is also made of a metal (e.g., stainless steel) or of a hard polymer material. The sonotrode portion in the most distal node position is preferably made of the same sonotrode material and is an integral part of the sonotrode. For further reducing friction between the sonotrode and the guide shaft, the most distal portion of the sonotrode at least including the most distal node position, or indeed the whole sonotrode, may be coated with a suitable friction reducing coating, which for a titanium sonotrode preferably consists of titanium nitride.

Furthermore, the distal sonotrode end, which constitutes an anti-node position, carries a ring that increases the sonotrode cross section and is made of a material being softer than the material of the guide shaft and softer than the sonotrode material. The distal ring is, e.g., made of a polymer, preferably of PEEK.

In most cases the cross sections of the sonotrode and the guide shaft through opening (bore) will be circular, but of course other cross section shapes are possible also, wherein, in any case, the mounting of the sonotrode within the guide shaft is to be as coaxial as possible such that equal radial clearance on all sides of the sonotrode is ensured as well as possible.

For systems including a sonotrode with an axial length corresponding to twice or three times or even more times the half wave length of the vibration to be transmitted by the sonotrode, it may be advantageous to not only equip the most distal node position in the above described manner but also one or possibly two node positions of further proximally situated sonotrode portions. The latter measure is advantageous in particular for very slender sonotrodes whose cross section does not or does only slightly increase from the distal towards the proximal sonotrode end.

BRIEF DESCRIPTION OF THE DRAWINGS

Exemplary embodiments of the invention are described in further detail in connection with the appended Figs., wherein:

FIG. 5 illustrates an application of the system according to the invention in a device suitable for reinforcing or augmenting the anchorage of e.g. a screw in a porous, fibrous or otherwise suitable material or in bone tissue of a patient.

FIG. 6 illustrates an application of the system according to the invention, in which a treatment element, e.g. a blade for cutting bone, is coupled to the distal end of the sonotrode.

DETAILED DESCRIPTION OF THE INVENTION

Figure 1:
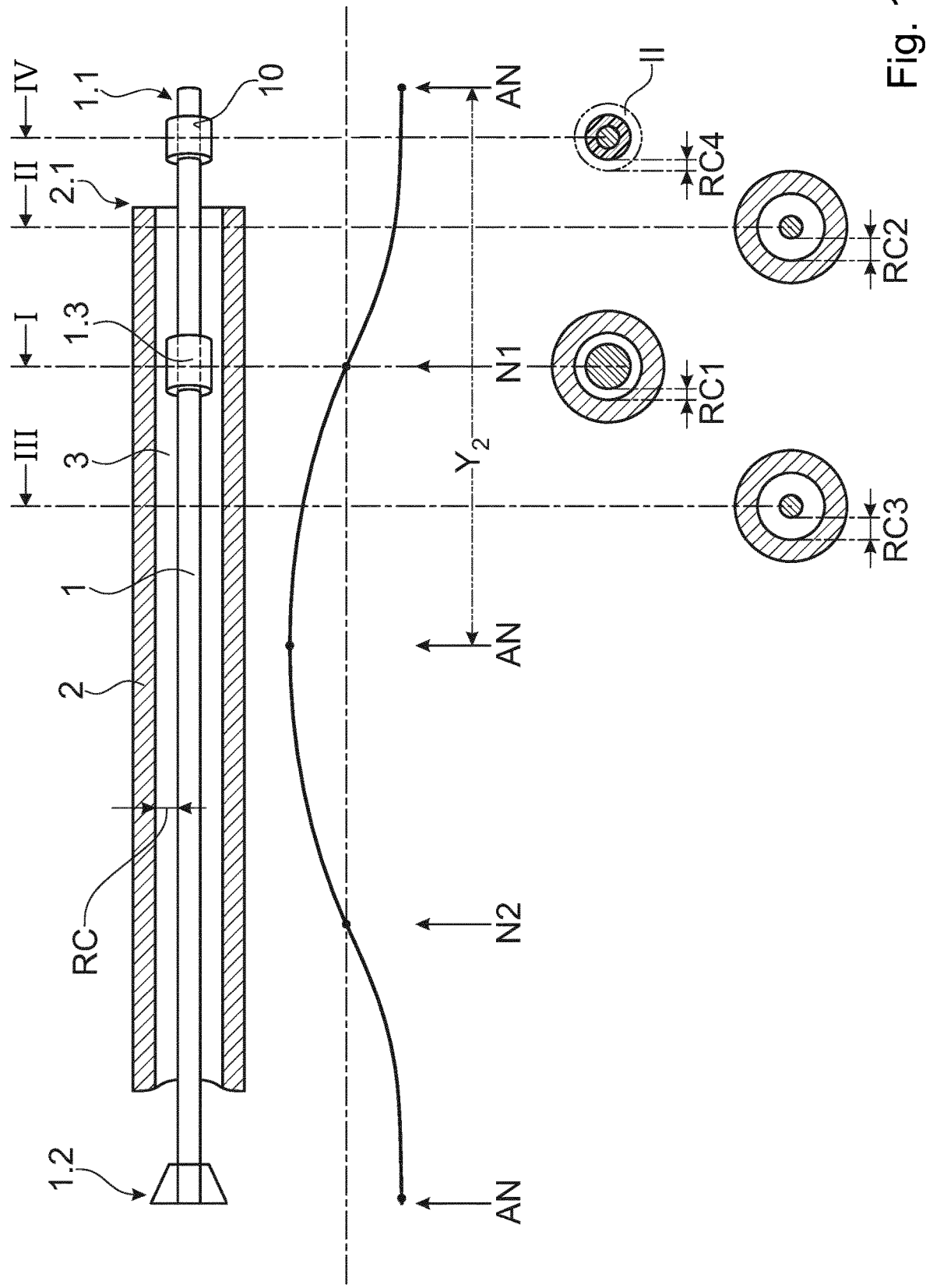
FIG. 1 shows an exemplary embodiment of the system according to the invention, wherein the upper half of FIG. 1 shows the system sectioned along its longitudinal axis together with a diagram of the stationary vibration wave in which the sonotrode of the system is operated, and wherein the lower half of FIG. 1 shows a plurality of cross sections through the system in differing positions along its length.

In all appended Figs., same reference numerals designate same elements or similar elements serving same functions.

FIG. 1 illustrates the system according to the invention by showing an exemplary embodiment thereof. The upper half of FIG. 1 shows the system sectioned along its longitudinal axis combined with the diagram of a corresponding stationary vibration wave in which the sonotrode is operated. The lower half of FIG. 1 shows, on a larger scale, a plurality of cross sections through the system in positions I, II, III and IV. The system includes a sonotrode 1 with a distal end 1.1 and a proximal end 1.2 and a guide shaft 2 with a distal end 2.1 and a proximal end (not shown), wherein, in operation, the proximal end 1.2 of the sonotrode 1 is coupled to a vibration source (e.g., transducer unit, not shown) and the proximal end of the guide shaft 2 may be coupled to a housing (not shown) in which the vibration source and the proximal end of the sonotrode may be arranged in a per se known manner. In an operating configuration of the system, the sonotrode 1 is positioned in a through opening 3 extending through the guide shaft 2.

As illustrated by the wave diagram, the sonotrode according to FIG. 1 has an axial length corresponding to twice one half of the wave length ($2 \times \lambda/2$), wherein the distal sonotrode end 1.1 and the proximal sonotrode end 1.2 constitute anti-node positions AN and there are two node positions N1 and N2 along the sonotrode length, the most distal node position being designated with N1. The guide shaft 2 is arranged for its distal end 2.1 to be positioned more distally than the most distal node position N.1 of the sonotrode 1, which is to be valid for all sonotrode positions in the guide shaft for applications in which the sonotrode 1 is arranged to be axially displaced in the guide shaft 2 during operation.

Figure 3:
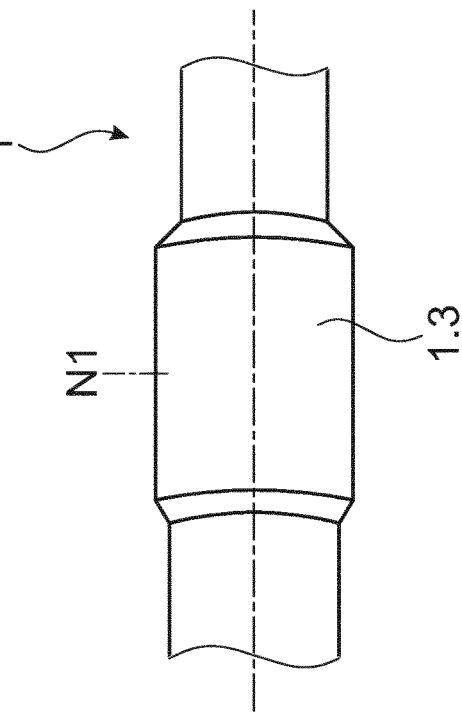
FIG. 3 shows on a larger scale the most distal node position or any other node position of an exemplary sonotrode suitable for the system according to the invention.

According to the invention, radial clearance RC between the sonotrode 1 and the guide shaft 2 is to be minimal in the most distal node position N1 of the sonotrode 1. This is achieved in particular for being applicable for an axially displaceable sonotrode, by the through opening 3 of the guide shaft 2 having, at least in a distal portion extending form a distal end portion to beyond the most distal node position N1 of the sonotrode 1, a constant cross section, and by the sonotrode 1 including a portion 1.3 of an increased cross section in the most distal node position N1 (see cross section in position I) as compared to the cross sections in positions II and III adjoining the distal node position N1 distally and proximally. Therein, as mentioned further above, the radial clearance between sonotrode 1 and guide shaft 2 may be smaller on the proximal side of the most distal node position N1 (cross section position III) than on the distal side of the most distal node position (cross section position II) by the sonotrode having correspondingly differing cross sections (see example as illustrated in FIG. 3).

Exemplary values for the radial clearance RC between sonotrode 1 and guide shaft 2 are for the most distal node position N1 a few hundredth of a mm (RC1: between 0.01 and 0.1 mm, preferably not more than 0.05 mm) and for positions II and III adjoining the most distal node position N1 about five to ten times more (RC2 and RC3: between 0.1 and 0.8 mm). The sonotrode portion of the most distal node position having an increased cross section has preferably an axial length which is no greater than 2 to 4% of half of the vibration wave length $\lambda/2$.

An exemplary embodiment of the system as illustrated in FIG. 1 includes a titanium sonotrode and a guide shaft of stainless steel, wherein the sonotrode to be operated at a vibration frequency in the range of 2 to 30 kHz, preferably 20 kHz, has an axial length of 245 mm and the guide shaft has a through bore with, at least in a distal portion of the guide shaft, a diameter of 3.1 mm. The sonotrode diameter is 3 mm in the most distal node position N1, 2.5 mm for a sonotrode portion adjoining the most distal node position distally (position II) and 2.65 mm for a sonotrode position adjoining the most distal node position proximally (position III). Therefore, the radial clearance RC is 0.05 mm (RC1) in the most distal node position, 0.3 mm (RC2) distally of the most distal node position N1 and 0.25 mm (RC3) proximally of the most distal node position N1.

The distal end 1.1 of the sonotrode as shown in FIG. 1 is equipped with a ring 10 of a polymer material, e.g., of PEEK, which is softer than the materials of the sonotrode and the guide tube, or the material of any further element which encloses the distal sonotrode end when in operation, and it has a larger cross section than the sonotrode cross section in positions adjoining the ring 10. A preferred material for the ring 10 is PEEK. The sonotrode distal end such equipped is particularly suitable for an apparatus as e.g. disclosed in the publication WO2011/054123 in which the sonotrode distal end is operated in the central bore of the cannulated screw, i.e., in a situation in which it is as tightly encapsulated as in the guide shaft, or in an apparatus in which a treatment element, e.g., a cutting blade, is coupled to the distal end of the of the sonotrode and the guide tube reaches as distally as possible, in particular to the antinode position of the sonotrode. It is preferably equipped in the same way if the vibrating sonotrode is to be withdrawn into the guide shaft for any given reason such that the distal sonotrode end is situated within the guide shaft. In all the named cases, the ring 10 prevents direct contact between and therewith wear of the sonotrode and the guide tube or any other element in which the distal sonotrode end is operated.

As seen from the cross section in position IV, the radial clearance RC4 between the ring 10 and an opening 11 of, e.g., a cannulated screw, in which the distal sonotrode end with the ring 10 is to operate, is advantageously in the same range as the radial clearance RC1 between the sonotrode and the guide shaft in the most distal node position N1 of the sonotrode.

Figure 2:
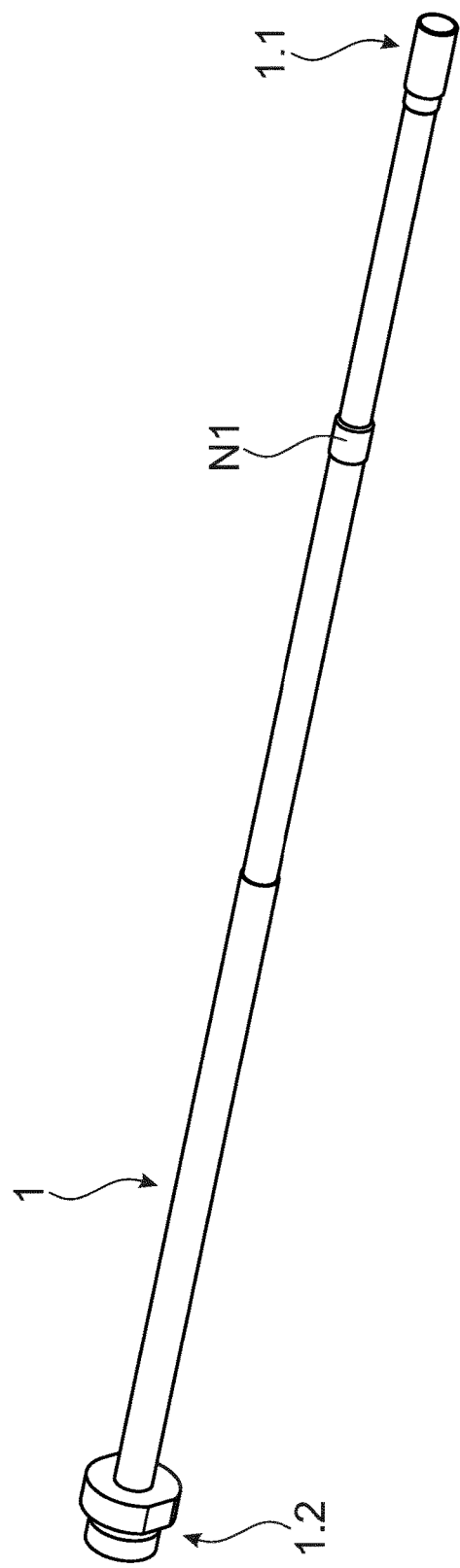
FIG. 2 is a three-dimensional illustration of the sonotrode of the system as show in FIG. 1

FIG. 2 is a three-dimensional representation on a more realistic scale of a sonotrode as described above in connection with FIG. 1. The lighter shade of the distal about half of the sonotrode represents a coating with a friction reducing coating of, e.g., titanium nitride. Such coating is in particular advantageous in the region of the most distal node position N1 and possibly at the distal sonotrode end, but may cover also the whole sonotrode.

FIG. 3 shows, on a larger scale than FIG. 1, the region of the most distal node position N1 of a sonotrode 1 that is suitable for a system according to the invention. The sonotrode portion 1.3 having an increased cross section is an integral part of the sonotrode and the transition to the neighboring sonotrode portions is, e.g., a 45° chamfer. The sonotrode is, e.g., fabricated from a rod having the increased cross section by correspondingly reducing the cross section of sonotrode portions other than the portion 1.3 using a lath.

Figure 4:
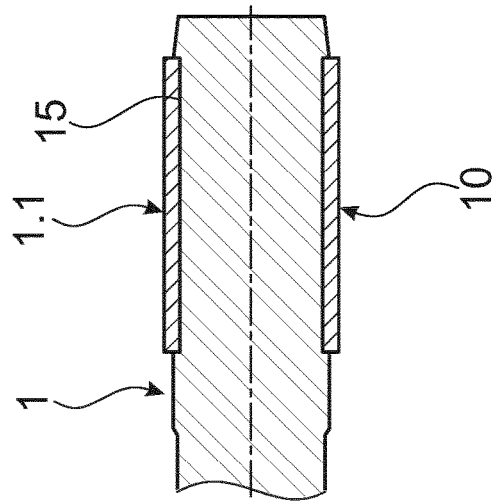
FIG. 4 shows on a larger scale the distal end (antinode position) of an exemplary sonotrode suitable for a system according to the invention.

FIG. 4 is an axial section through an exemplary distal end 1.1 of a sonotrode 1 suitable for the system according to the invention. As discussed already in connection with FIG. 1 the distal sonotrode end is equipped with a ring 10 of a polymer material which has a sufficient resiliency for being able to be mounted in a circumferential groove 15 provided on the sonotrode. This measure keeps the ring 10 in a form fitting manner in position and prevents inadvertent removal. For designing and dimensioning the ring 10 and its fixation on the sonotrode end, the high axial acceleration forces acting on the ring when the sonotrode is vibrated and, for medical applications, also sterilization temperatures have to be taken into account. Experience shows that for safely keeping the ring 10 in the groove, it is necessary to dimension ring and groove either for a clearance fit in a relatively deep groove (form fit only) or for a press-fit (in addition to the form fit). Therein, the press-fit alternative is easier to be established but may be prone to relaxation, in particular for medical applications and therewith multiple sterilization at elevated temperatures. A suitable material for the press-fit alternative is therefore, e.g., a high temperature thermoplastic material such as, e.g., PEEK. For the clearance-fit alternative, relaxation is no problem and mounting the ring on the sonotrode end is easier, but a material with a higher elasticity is needed, such as, e.g., a hard elastomere, e.g., highly cross-linked polyurethane.

For specific applications it may be sufficient to mount the ring 10 without providing a groove on the sonotrode end. In such a case, the ring is press-fitted onto the sonotrode end and/or is fixed with the aid of a suitable adhesive.

FIG. 5 illustrates a preferred application of the system according to the invention in a device which is applicable for reinforcing or augmenting the anchorage of, e.g., a screw in a porous or fibrous or otherwise suitable material or in bone tissue of a patient. The named reinforcement or augmentation is achieved with the aid of a material having thermoplastic properties and vibration energy, in particular ultrasonic vibration energy, wherein the material having thermoplastic properties being initially solid is positioned in a corresponding space within the screw, is compressed against the inside of the screw and the vibration energy is applied to it. This leads to liquefaction of at least part of the material having thermoplastic properties and to displacement of the liquefied material through apertures in the screw wall where it gets into contact with or interpenetrates the material in which the screw has been pre-anchored to start with.

FIG. 5 shows in an axial section a distal part of a hand piece suitable for the named reinforcing or augmenting process. The screw 20 is a cannulated screw and includes a suitable fenestration connecting a central, distally at least partly closed canal with the threaded outer screw surface. A pin 21 including the material having thermoplastic properties is situated within the screw canal. The screw is in particular a poly-axial pedicle screw and comprises, coupled to its head in a freely rotatable and pivoting manner, a receiving piece 22 which eventually serves for mounting, e.g., a rod to the anchored screw. For the reinforcing or augmenting process, the screw is mounted to an ultrasonic hand piece of which FIG. 5 only shows a distal housing part including an outer shaft 25, an inner shaft 26, and a sonotrode 30 reaching through the inner shaft into the screw 20. A proximal sonotrode end 31 is connected in a per se known manner to a vibration source (not shown) situated in an only partly shown proximal housing part 32. The proximal housing part 32 also contains a driver spring (not shown) which biases the sonotrode towards the screw. The sonotrode 30 and the inner guide shaft 26 constitute together a system according to the invention, and they are equipped as shown in FIG. 1 (details not visible due to small scale).

When the device as partly shown in FIG. 5 is assembled and ready for the reinforcing or augmenting process, it constitutes a closed load frame in which the pin 21 of the material having thermoplastic properties is compressed between the distal sonotrode end and the bottom of the canal in the screw. On activation of the vibration, the material having thermoplastic properties is at least partly liquefied and pressed out of the screw 20. For keeping up the compression force on the pin 21 and for compensating its length reduction through the displacement of the liquefied material, the sonotrode 30 is driven in a distal direction relative to the inner (guide) shaft.

In particular, for being able to handle known poly-axial pedicle screws and for being applicable in minimally invasive surgery, the sonotrode and the guide shaft being parts of the device as illustrated in FIG. 5 have dimensions as discussed further above, wherein the bore of the guide shaft or at least a most distal portion thereof has preferably a similar cross section as the canal of the screw. Even though the screw parts are attached to the distal end of the double guide shaft and are axially tensioned against each other and therewith aligned coaxially, slight diversions from an absolute coaxiality cannot be fully prevented. This means that equipping the sonotrode not only with the portion of increased cross section in the region of the most distal node position but also with the ring at its distal end renders operation of the system more problem-free and gives the system a longer life.

Obviously, instead of a screw, any suitably perforated or fenestrated sleeve can be handled with the device according to FIG. 5 with the integrated system according to the invention if suitable coupling means for coupling the sleeve to the distal housing part are provided.

Further details regarding the device as in part illustrated in FIG. 5 can be taken from the co-pending application with the title "System and method for establishing an anchorage or reinforcement in an object with the aid of in situ liquefaction and displacement of a material having thermoplastic properties" by the same applicant.

FIG. 6 illustrates a further application of the system of sonotrode 1 and guide shaft 2 according to the invention. The application concerns a sonotrode with a treatment element coupled to the distal end thereof, the treatment element being suitable for any medical or non-medical treatment such as, e.g., cutting, grinding, rasping, drilling, punching, rubbing, cleaning, cauterizing, etc.

FIG. 6 is an axial section and shows a distal portion of the sonotrode 1, which is adapted to a selected vibration frequency to vibrate with an anti-node position A at its distal end and a node position N distanced therefrom in a proximal direction. The sonotrode 1 extends in a guide shaft 2.

Further shown is a treatment element in form of a cutting blade 40 with a proximal coupling portion 41, an intermediate transition portion 42 and a distal blade portion 43. The coupling portion 41, which is equipped for coupling to the distal end of the sonotrode 1, the coupling being equipped for as loss free transmission of the vibration energy and, e.g., by including a threaded bolt (not shown) carried by the coupling portion 41 and cooperating with a corresponding threaded blind bore in the distal face of the distal sonotrode end. The coupling portion 41 has e.g. about the same cross section as the distal end of the sonotrode 1. The blade portion 43 is blade-shaped with a narrow rectangular cross section and it possibly has sharp or serrated lateral and or distal cutting edges. For being able to be used also as a grinding tool, the lateral surfaces of the blade portion 43 may be rough or equipped with a grinding surface structure. The transition portion 42 is laterally tapering from a cross section adapted to the coupling portion 41 to the cross section of the blade portion 43. Preferably the cutting blade is integrally formed as one piece.

The guide shaft 2 reaches distally to cover the distal end of the sonotrode 1 and possibly also the coupling portion 41 of the cutting blade 40. As discussed further above, the sonotrode 1 is equipped with a portion 1.3 of a larger cross section in the node position N and with a ring 10 mounted to its distal end portion (anti-node position A).

As discussed in connection with the application of the inventive system according to FIG. 5, also in the application as illustrated in FIG. 6 the ring 10 in the distal anti-node position helps relevantly to prevent operation problems due to misalignment of the sonotrode and the guide shaft, which may occur specially when the treatment carried out with the aid of the system causes lateral forces acting on the treatment element. This may, e.g., be the case, when the blade portion is equipped with lateral grinding surfaces and is used for grinding by pressing one of the grinding surfaces of the vibrating blade against an object and simultaneously carrying out a grinding movement.

Further details regarding cutting blades with or without grinding surfaces and being suitable for use in connection with a system of sonotrode and guide shaft according to the invention are found in the co-pending application titled "Device and method for perforation a dense bone layer" by the same applicant.

What is claimed is:

1. A system to be used for transmitting ultrasonic vibration, the system comprising a sonotrode and a guide shaft,
    wherein the sonotrode has a distal end and a proximal end and is designed to vibrate in a stationary wave with a wave length and comprising at least one node position between the distal end and the proximal end and an anti-node position at the distal end,
    wherein the guide shaft has a distal end and a proximal end and a through opening extending from the distal end to the proximal end,
    wherein, for operation, the sonotrode extends through the through opening of the guide shaft with a radial clearance and the distal end of the guide shaft is situated on a distal side of a most distal one of the at least one node position of the sonotrode,
    wherein the sonotrode comprises a portion of an increased cross section at the most distal node position, the portion being an integral part of the sonotrode and being made of the same material as the sonotrode so that the radial clearance between the sonotrode and the guide shaft is a minimum radial clearance at the portion at the most distal node position,
    wherein the distal end of the sonotrode is equipped with a polymer ring mounted at the anti-node position at the distal end and situated in a circumferential groove of the sonotrode in a way radially protruding from the sonotrode, and
    wherein the sonotrode is axially slidable relative to the guide shaft between a first position where the sonotrode protrudes from the distal end of the guide shaft such that the polymer ring mounted at the anti-node position is beyond the distal end of the guide shaft and a second position where the sonotrode is withdrawn into the guide shaft such that the polymer ring mounted at the anti-node position is radially disposed between the sonotrode and the guide shaft and wherein, for operation, a permeable sleeve or a cannulated screw is connected to the distal end of the guide shaft, the permeable sleeve encasing the distal end of the sonotrode.

2. The system according to claim 1, wherein the distal end of the guide shaft has substantially the same axial position as the distal end of the sonotrode or reaches distally beyond the distal end of the sonotrode, and wherein a treatment element is coupled to the distal end of the sonotrode.

3. The system according to claim 1, wherein said sonotrode portion comprising the most distal node position has a larger cross section than adjoining sonotrode portions, and wherein the through opening of the guide shaft comprises a distal portion of a constant cross section, in which during all operation said sonotrode portion comprising the most distal node position is situated.

4. The system according to claim 1, wherein said sonotrode portion comprising the most distal node position is an integral part of the sonotrode.

5. The system according to claim 1, wherein the length of the sonotrode corresponds to two or three times one half of said wave length.

6. The system according to claim 1, wherein the minimum radial clearance is in the range of 0.01 to 0.1 mm.

7. The system according to claim 1, wherein radial clearance between the sonotrode and the guide shaft in a position distally adjoining said sonotrode portion comprising the most distal node position is larger than in a position proximally adjoining said sonotrode portion comprising the most distal node position.

8. The system according to claim 1, wherein the sonotrode and the through opening of the guide shaft have substantially circular cross sections.

9. The system according to claim 1, wherein the sonotrode is made of titanium and/or wherein the guide shaft is made of stainless steel.

10. The system according to claim 1, wherein said sonotrode portion comprising the most distal node position has a diameter of 3 mm and a distal portion of the guide shaft comprises a through bore of 3.1 mm diameter.

11. The system according to claim 10, wherein a sonotrode portion adjoining said sonotrode portion comprising the most distal node position has a diameter of 2.5 mm and a distal portion of the guide shaft comprises a through bore of 3.1 mm diameter.

12. The system according to claim 1, wherein the polymer ring is made of PEEK or of polyurethane.

13. A sonotrode being part of a system according to claim 1.

14. The sonotrode according to claim 13, and further comprising a treatment element coupled to its distal end.

15. The sonotrode according to claim 14, wherein the treatment element is a cutting blade.

16. The sonotrode according to claim 15, wherein the cutting blade comprises lateral surfaces being equipped for grinding or rasping by being rough or by comprising a corresponding surface structure.

17. The system according to claim 1 in a device for reinforcing or augmenting a cannulated and fenestrated screw or permeable sleeve with the aid of a material having thermoplastic properties and vibrational energy.

18. A system to be used for transmitting ultrasonic vibration, the system comprising a sonotrode and a guide shaft, wherein the sonotrode has a distal end and a proximal end and is designed to vibrate in a stationary wave with a wave length and comprising at least one node position between the distal end and the proximal end and an anti-node position at the distal end, wherein the guide shaft has a distal end and a proximal end and a through opening extending from the distal end to the proximal end, wherein, for operation, the sonotrode extends through the through opening of the guide shaft with a radial clearance and the distal end of the guide shaft is situated on a distal side of a most distal one of the at least one node position of the sonotrode, and wherein the sonotrode comprises a portion of an increased cross section in the most distal node position, the portion being an integral part of the sonotrode made of the same sonotrode material so that the radial clearance between the sonotrode and the guide shaft is a minimum radial clearance for said sonotrode portion in the most distal node position, and wherein the distal end of the sonotrode is equipped with a polymer ring mounted at the anti-node position at the distal end and situated in a circumferential groove of the sonotrode in a way radially protruding from the sonotrode, wherein the minimum radial clearance is in the range of 0.01 to 0.1 mm and wherein radial clearance between the sonotrode and the guide shaft in positions adjoining said sonotrode portion comprising the most distal node position is about five to ten times larger than said minimum radial clearance.

* * * * *